(12) United States Patent
Yang

(10) Patent No.: US 7,074,207 B2
(45) Date of Patent: Jul. 11, 2006

(54) SAFETY SYRINGE

(76) Inventor: Chung-Yu Yang, 5F, No. 396, Chih-Hu Rd., Nei-Hu Dist., Taipei City (TW)

(*) Notice: Subject to any disclaimer, the term of this patent is extended or adjusted under 35 U.S.C. 154(b) by 677 days.

(21) Appl. No.: 10/347,800

(22) Filed: Jan. 22, 2003

(65) Prior Publication Data

US 2003/0163094 A1 Aug. 28, 2003

Related U.S. Application Data

(63) Continuation-in-part of application No. 09/931,014, filed on Aug. 17, 2001, now abandoned.

(51) Int. Cl.
*A61M 5/00* (2006.01)

(52) U.S. Cl. .................... 604/110; 604/195
(58) Field of Classification Search ........... 604/110, 604/241, 218, 198, 240, 181, 187, 195, 197, 604/263

See application file for complete search history.

(56) References Cited

U.S. PATENT DOCUMENTS

| 4,828,548 A | 5/1989 | Walter | 604/164 |
| 5,114,410 A * | 5/1992 | Caralt Batlle | 604/195 |
| 5,395,337 A | 3/1995 | Clemens et al. | 604/110 |
| 6,077,245 A | 6/2000 | Heinrich et al. | 604/110 |

FOREIGN PATENT DOCUMENTS

| WO | WO 95/31236 | 11/1995 |
| WO | WO 95/31236 A1 | 11/1995 |

* cited by examiner

*Primary Examiner*—Nicholas D. Lucchesi
*Assistant Examiner*—Kevin C. Sirmons
(74) *Attorney, Agent, or Firm*—Bacon & Thomas

(57) ABSTRACT

A safety syringe includes a flexible holder-supporting seat that is sleeved around and that clamps a needle holder within a front end portion of a syringe barrel. A flexible sealing member seals an open front end of a plunger so as to define a vacuum chamber in the plunger. When the plunger moves within the barrel to a front limit position, a holder-retaining front portion of the sealing member engages and retains the needle holder thereon, and the plunger pushes the holder-supporting seat to separate from the needle holder such that the sealing member and the needle holder move rearward within the syringe barrel due to negative pressure produced in the plunger, thereby retracting a needle into the syringe, barrel.

5 Claims, 12 Drawing Sheets

SAFETY SYRINGE

CROSS REFERENCE TO RELATED APPLICATION

This is a Continuation-in-Part (CIP) of U.S. patent application Ser. No. 09/931,014, filed on Aug. 17, 2001 now abandoned.

BACKGROUND OF THE INVENTION

1. Field of the Invention

This invention relates to a medical syringe, more particularly to a safety syringe with an automatically retractable needle.

2. Description of the Related Art

After using a disposable medical syringe, the user may be injured by accidental puncture of a needle of the syringe. PCT Application No. 000287 and U.S. Pat. Nos. 5,395,337 and 6,077,245 disclose safety syringes that are provided with retractable needles, which can be withdrawn into syringe barrels or plungers by means of a negative pressure or a spring force to prevent accidental puncture. However, the structures of the aforesaid conventional safety syringes are too complex to fabricate at relatively low costs.

SUMMARY OF THE INVENTION

The object of this invention is to provide a safety syringe, which includes a retractable needle and which has a relatively simple structure.

According to this invention, a safety syringe includes a flexible holder-supporting seat that clamps a needle holder within a front end portion of a syringe barrel. A flexible sealing member seals an open front end of a plunger so as to define a vacuum chamber in the plunger. When the plunger moves within the syringe barrel to a front limit position, a holder-retaining front portion of the sealing member engages and retains the needle holder thereon, and the plunger pushes the holder-supporting seat to separate from the needle holder such that the sealing member and the needle holder move rearward within the syringe barrel due to negative pressure produced within the plunger, thereby retracting a needle into the syringe barrel

BRIEF DESCRIPTION OF THE DRAWINGS

These and other features and advantages of this invention will become apparent in the following detailed description of the preferred embodiments of this invention, with reference to the accompanying drawings, in which.

DETAILED DESCRIPTION OF THE PREFERRED EMBODIMENTS

Figure 1:
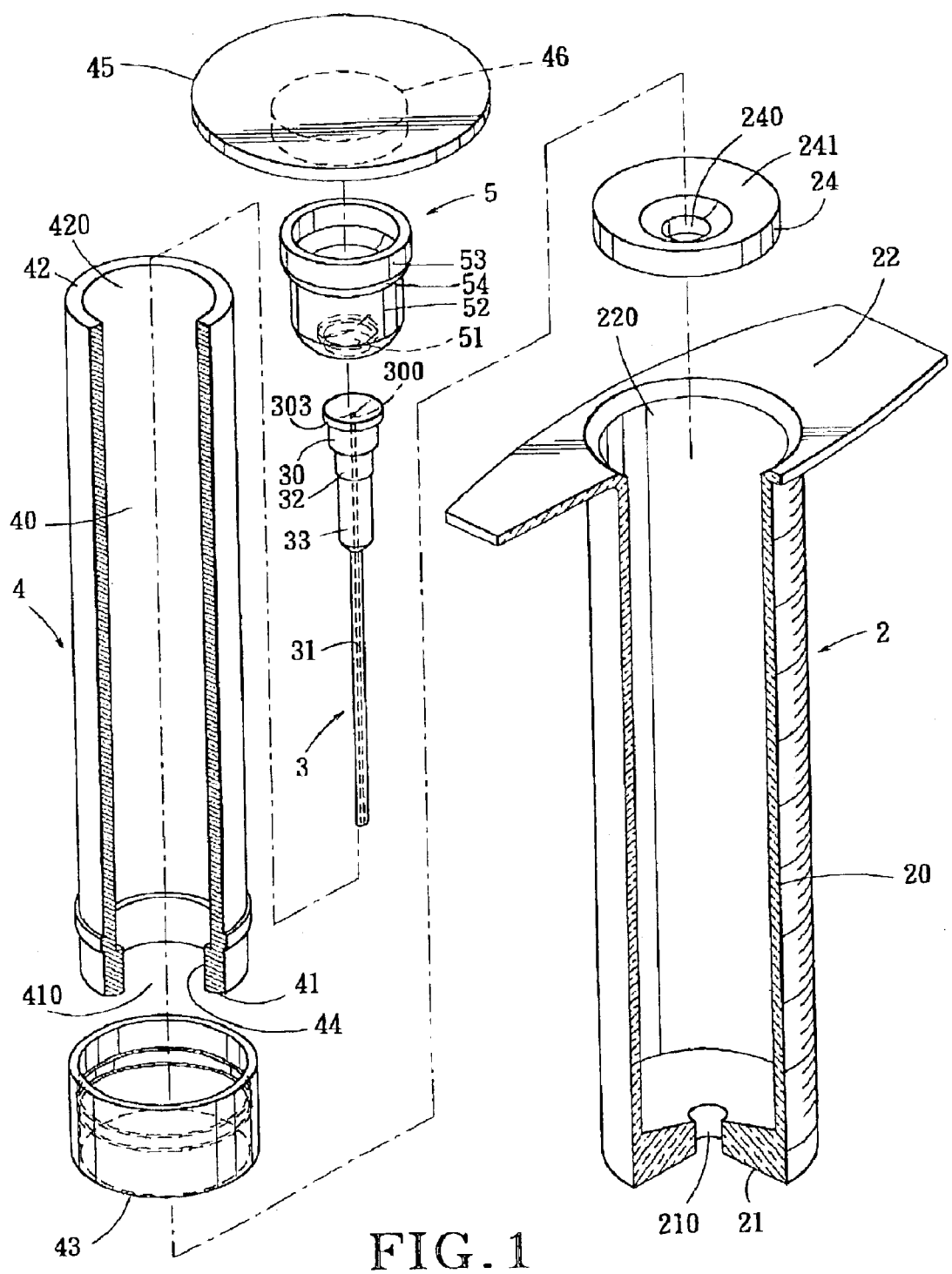
FIG. 1 is an exploded perspective view of a first preferred embodiment of a safety syringe according to this invention.
Figure 2:
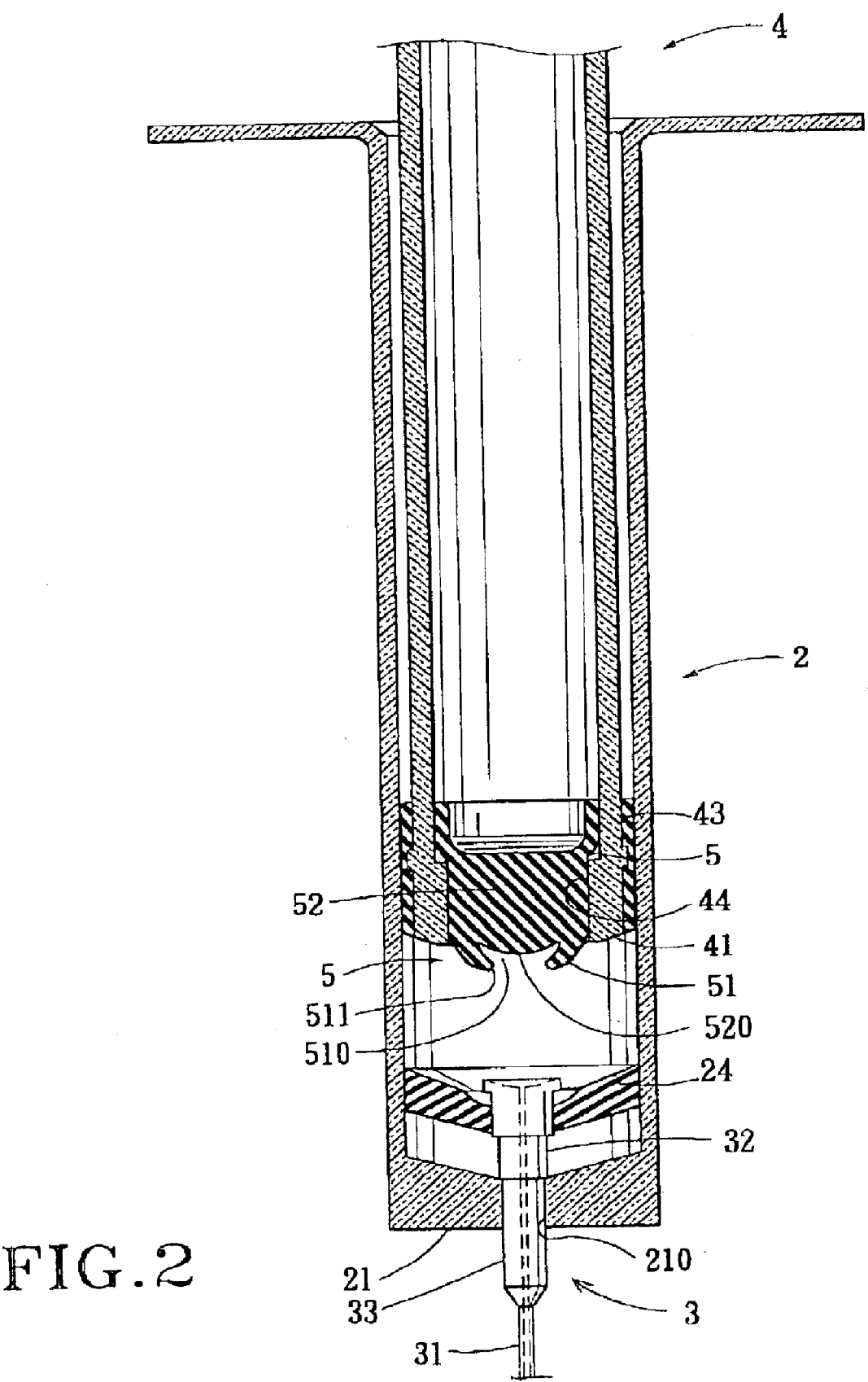
FIG. 2 is a sectional view of the first preferred embodiment.
Figure 3:
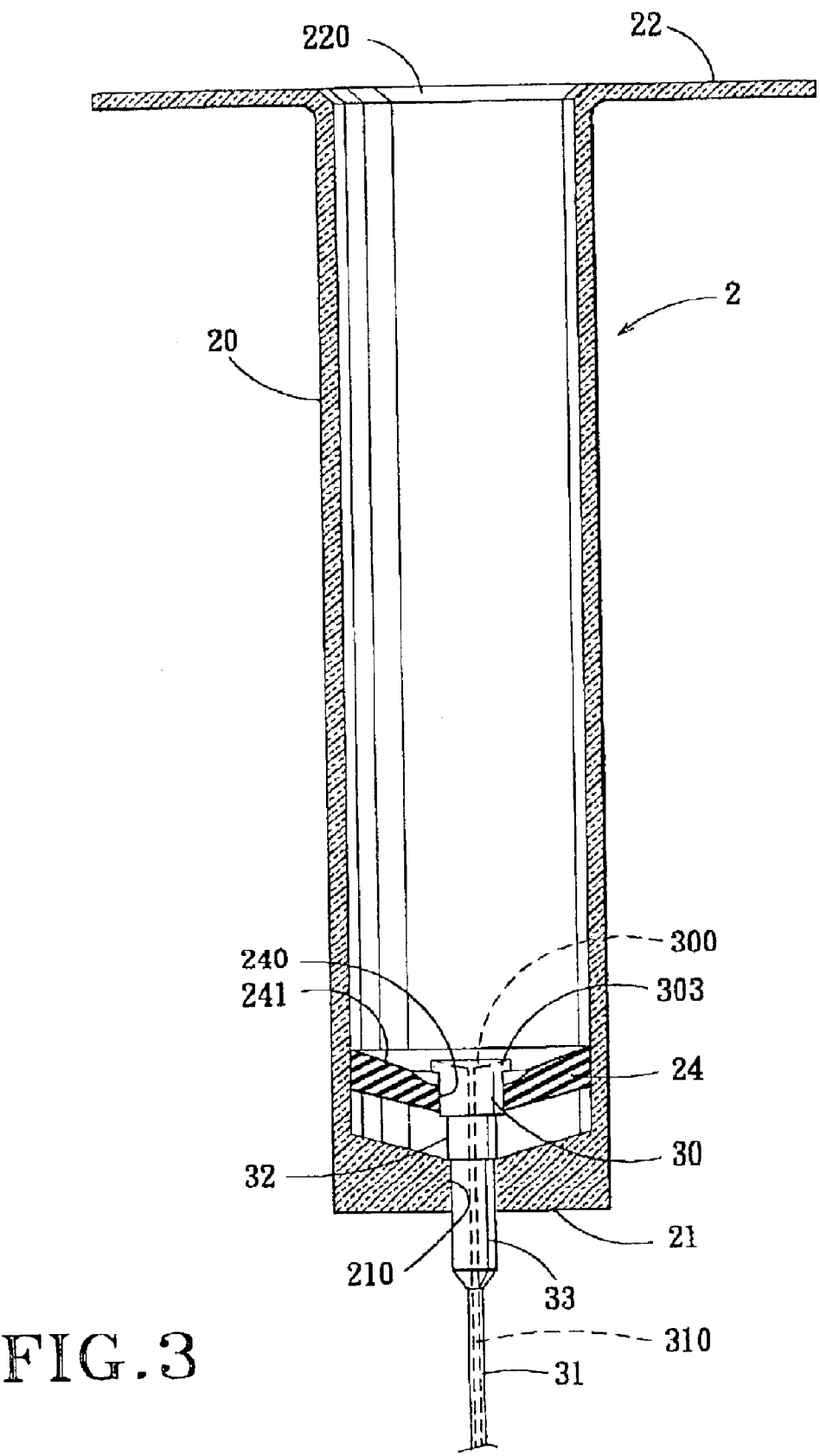
FIG. 3 is a sectional view of a syringe barrel and a needle unit of the first preferred embodiment.
Figure 4:
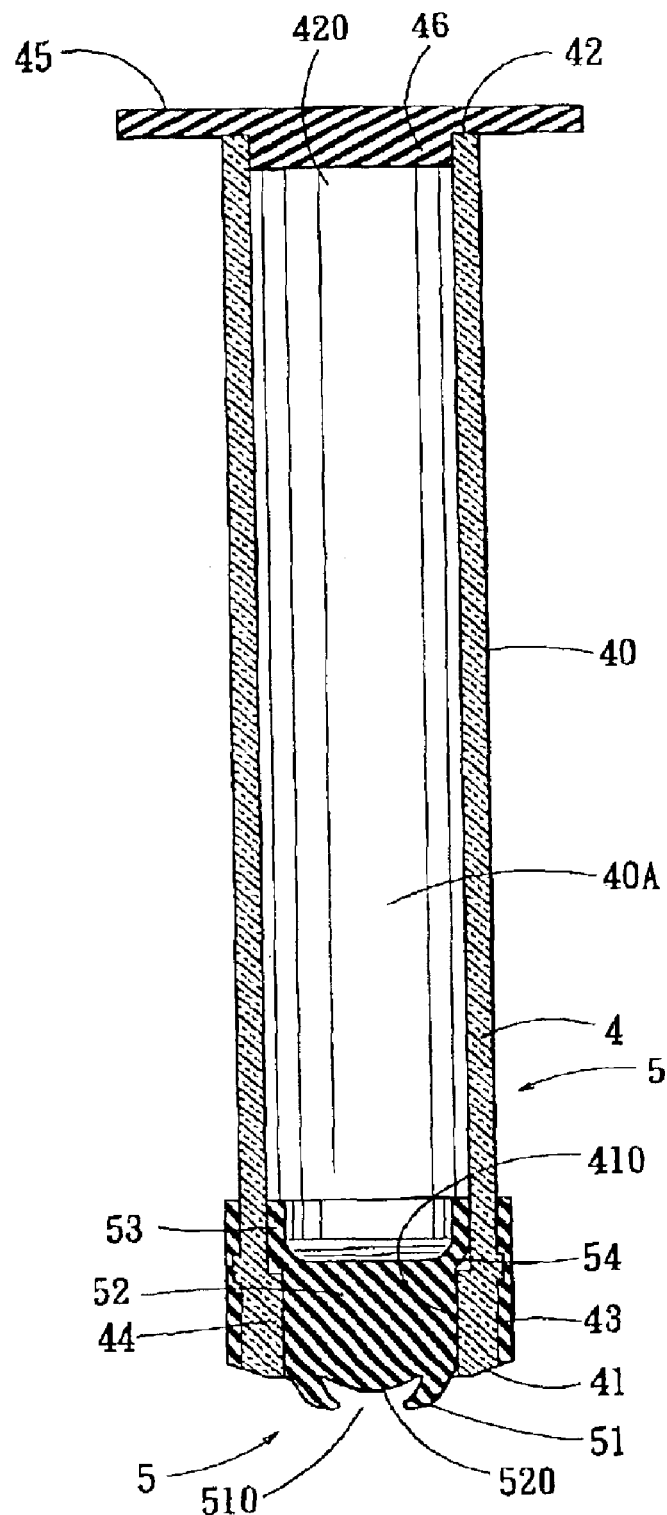
FIG. 4 is a sectional view of a plunger and a sealing member of the first preferred embodiment.

Referring to FIGS. 1, 2, 3, and 4, a first preferred embodiment of a safety syringe according to this invention is shown to include a syringe barrel 2, a needle unit 3, a plunger 4, and a flexible sealing member 5. The needle unit 3 has a needle holder 30, a needle 31, a spacer portion 32 having a rear end that is formed integrally with a front end of the needle holder 30, and a connecting portion 33 having a front end that is formed integrally with a rear end of the needle 31, and a rear end that is formed integrally with a front end of the spacer portion 32.

The syringe barrel 2 includes a barrel body 20, a front end wall 21 that is formed integrally with a front end of the barrel body 20 and that has a front opening 210, a rear end wall 22 that is formed integrally with a rear end of the barrel body 20 and that has a rear opening 220, and an annular flexible holder-supporting seat 24 with frustoconical front and rear end surfaces 241, each of which has a diameter that increases rearward. The holder-supporting seat 24 is sleeved on the needle holder 30, and has a central hole 240 formed therethrough, an outer periphery that is in frictional contact with an inner surface of the syringe barrel 2 in such a manner that a liquid-tight seal is established therebetween, and an inner periphery that is in frictional contact with an outer surface of the needle holder 30 of the needle unit 3 in such a manner that a liquid-tight seal is established therebetween.

The needle unit 3 is inserted into the syringe barrel 2 through the rear opening 220. The connecting portion 33 of the needle unit 3 extends through the front opening 210 in the syringe barrel 2. The needle 31 is exposed outwardly from the front opening 210. The spacer portion 32 is sized to prevent movement of the spacer portion 21 into the front opening 210. As such, the needle holder 30 is clamped within the central hole 240 in the holder-supporting seat 24 at a position that is spaced apart from the front end wall 21 at a predetermined distance. The needle holder 30 has a rear end that is formed with an outward flange 303 which extends integrally, radially, and outwardly therefrom and which is sized to prevent forward movement of the outward flange 303 into the central hole 240 in the holder-supporting seat 24.

The plunger 4 is disposed movably within the syringe barrel 2, and includes a plunger body 40 that has an open front end 41 which is formed with a front opening 410 so that the sealing member 5 can be placed into the barrel body 40 and can extend therethrough during assembly, and an open rear end 42 that is formed with a rear opening 420. A unitary rear end wall 45 has a circular projection 46 extending forwardly therefrom and press-fitted within the rear opening 420 in the barrel body 40. When the plunger 4 is to be evacuated, the rear end wall 45 can be removed from the plunger body 40 for evacuation of air from the plunger 4. A rubber seal ring 43 is disposed between the plunger 4 and the syringe barrel 2 so as to establish a liquid-tight seal therebetween. The plunger body 40 has a front end that is formed with an inward flange 44 extending integrally, radially, and inwardly therefrom.

The sealing member 5 is disposed movably within the front end portion of the plunger 4 so as to define a vacuum chamber (40A) in the plunger 4 between the sealing member 5 and the rear wall 45. The sealing member 5 is unitary, is made of rubber, and includes a holder-retaining front portion 51 disposed behind and spaced apart from the needle holder 30, a sealing rear portion 52 for closing the front opening 410 in the plunger 4, a rear end skirt portion 53, and a shoulder 54 defined between the sealing rear portion 52 and the skirt portion 53. The inward flange 44 of the plunger 4 is sleeved around and clamps the sealing rear portion 52 of the sealing member 5 in the plunger 4 so as to prevent movement of the sealing member 5 relative to the plunger 4, thereby permitting synchronous rearward movement of the sealing member 5 and the plunger 4 when the plunger 4 is pulled rearward relative to the syringe barrel 2. The holder-retaining front portion 51 is shaped as an annular flange that extends forward and inwardly to define a blind hole 510 and that has a rounded front end edge 511 for guiding movement of the outward flange 303 of the needle holder 30 into the blind hole 510 when the outward flange 303 moves into the blind hole 510. The blind hole 510 has a front end that has a diameter which is slightly smaller than that of the outward flange 303 so as to confine the outward flange 303 within the blind hole 510. The holder-retaining front portion 51 is formed with a curved projection 520 that is located within the blind hole 510 and that is movable within the syringe barrel 2 to seal the rear opening 300 in the needle holder 30 when the outward flange 303 engages the blind hole 510.

Figure 5:
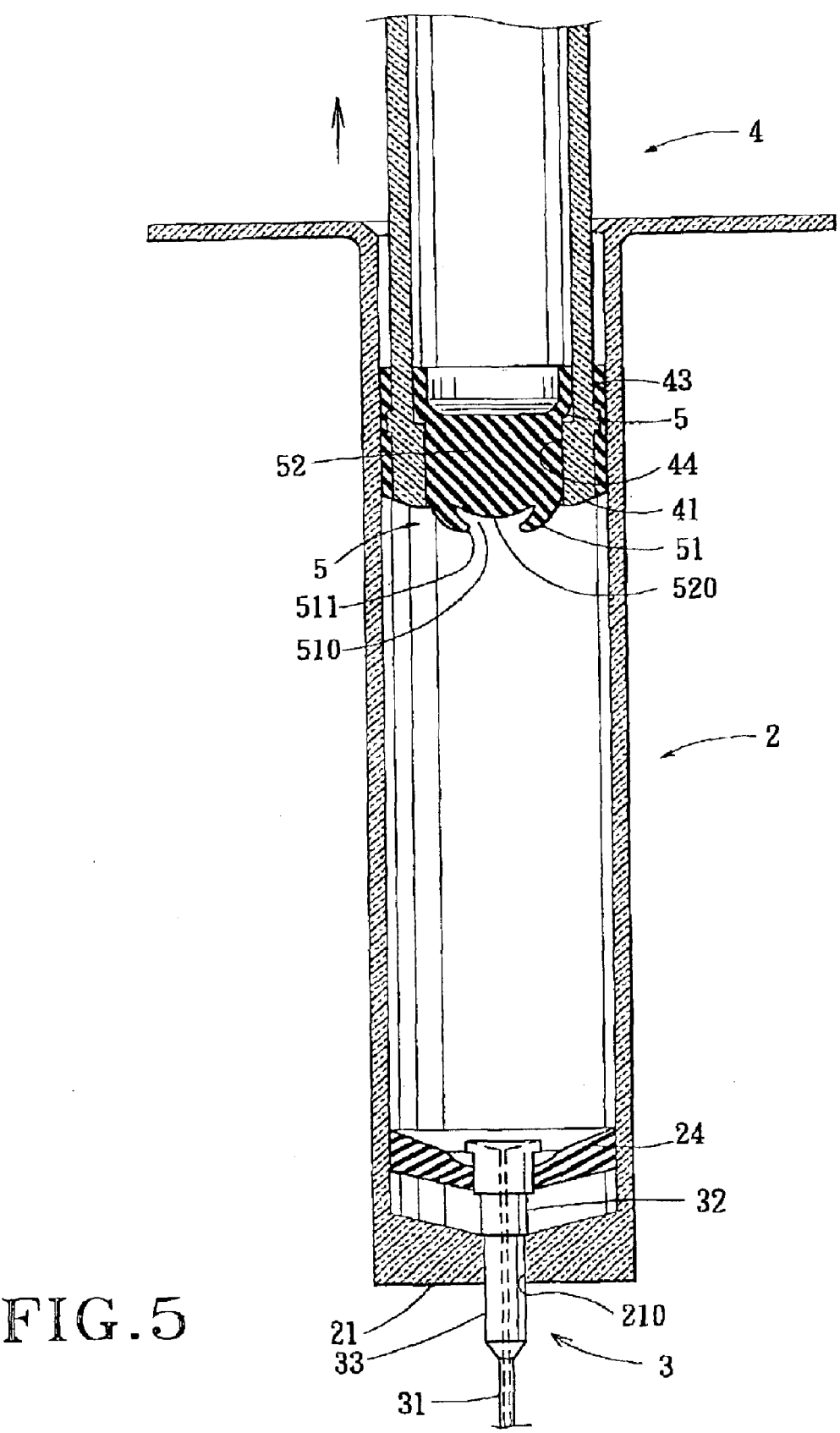
FIG. 5 illustrates how the sealing member is moved together with the plunger when the plunger is pulled rearward relative to the syringe barrel.

Referring to FIG. 5, when the plunger 4 is pulled rearward relative to the syringe barrel 2 in order to draw a medical liquid, blood, or body liquid from a subject, a rear edge of the inward flange 44 of the plunger 4 engages the shoulder 54 of the sealing member 5 so as to permit synchronous movement of the sealing member 5 and the plunger 4.

Figure 6:
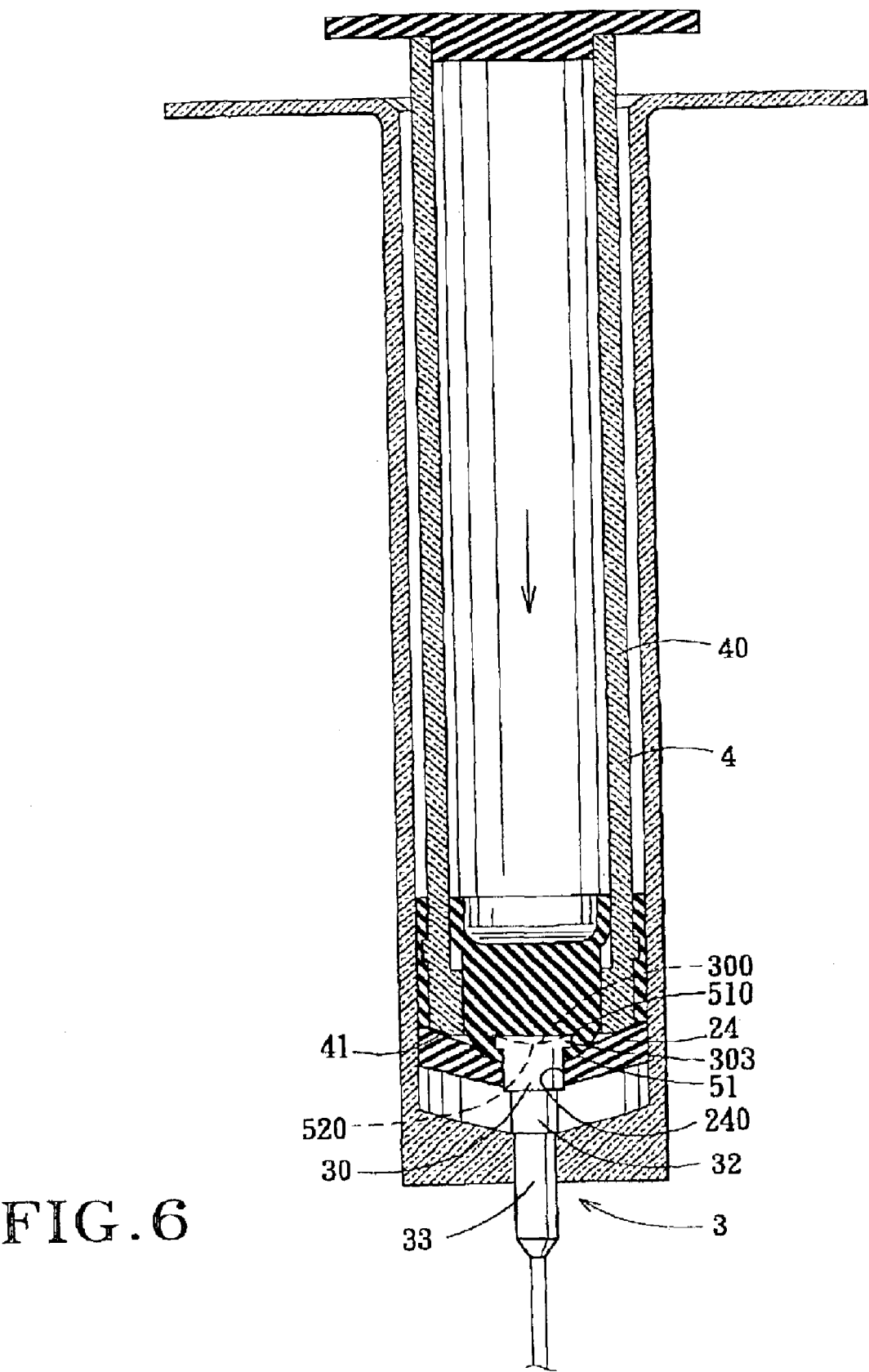
FIG. 6 illustrates how a holder-retaining front portion of the sealing member of the first preferred embodiment engages a needle holder.
Figure 7:
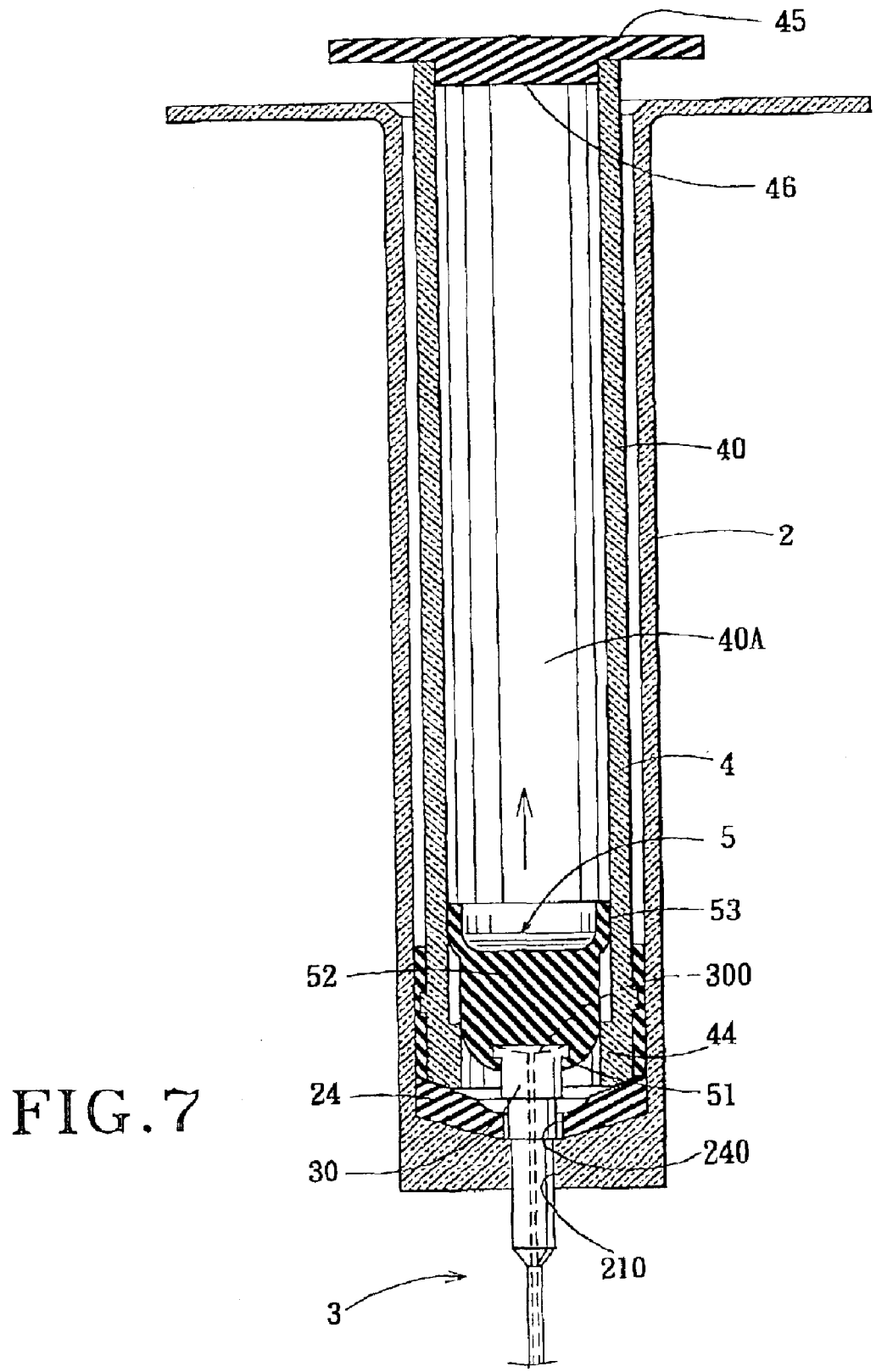
FIG. 7 illustrates how a holder-supporting seat of the first preferred embodiment is pushed by the plunger to separate from the needle holder.
Figure 8:
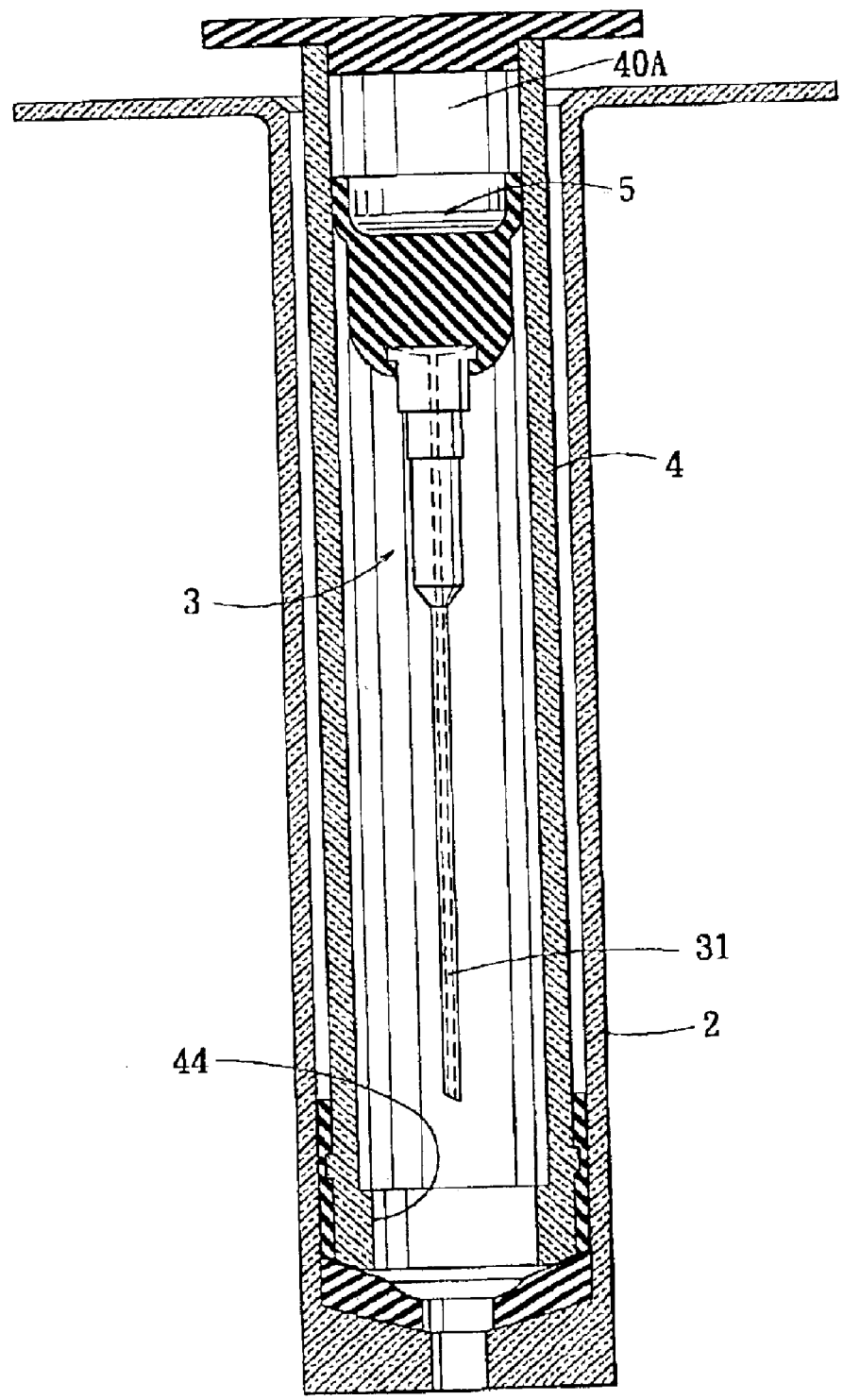
FIG. 8 illustrates how the needle unit of the first preferred embodiment is retracted into the plunger.

When it is desired to inject a medical liquid into a body, the plunger 4 is moved to a position shown in FIG. 6, where the outward flange 303 of the needle holder 30 engages the blind hole 510 in the sealing member 5, and where a front end of the plunger body 40 comes into contact with the holder-supporting seat 24. Thereafter, the sealing member 5 is blocked by the needle holder 30 from further forward movement within the syringe barrel 2. The plunger 4 continues to move forward within the syringe barrel 2 to a front limit position shown in FIG. 7, where the holder-supporting seat 24 is pushed by the plunger 4 to separate from the needle holder 30 and where the rear sealing rear portion 52 of the sealing member 5 is released from the inward flange 44 of the plunger 4. As such, an assembly of the sealing member 5 and the needle unit 3 will move rearward within the plunger 4 due to negative pressure produced within the evacuated plunger 4 until it moves to a retracted position shown in FIG. 8, where the needle unit 3 is concealed within the plunger 4.

Figure 9:
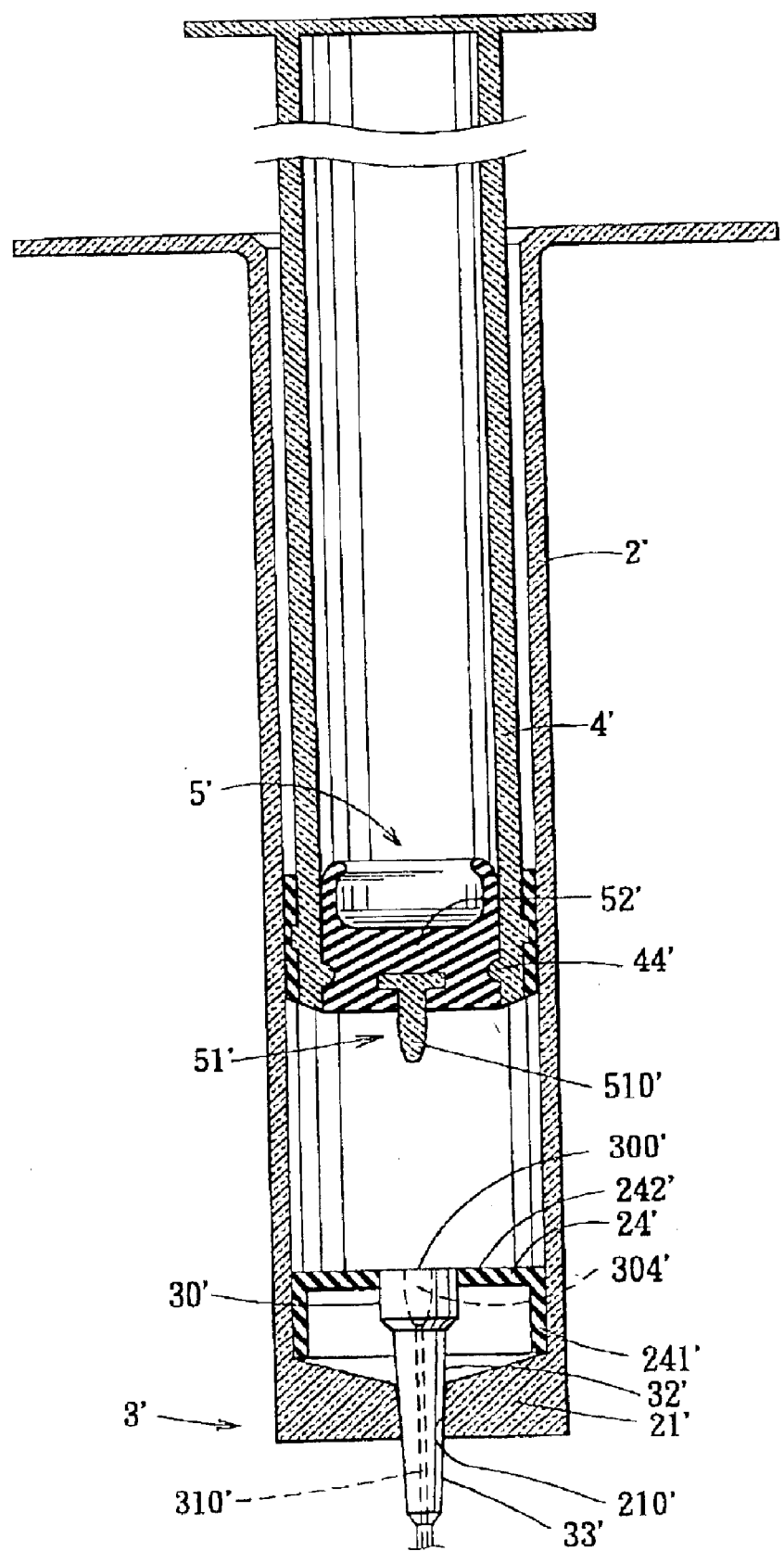
FIG. 9 is a sectional view of a second preferred embodiment of a safety syringe according to this invention.

Referring to FIG. 9, a second preferred embodiment of a safety syringe according to this invention is shown to include a syringe barrel 2', a needle unit 3', a plunger 4', and a sealing member 5'. The differences between the first and second preferred embodiments are described in the succeeding paragraph.

The syringe barrel 2' includes a flexible holder-supporting seat 24' constructed as a hollow cylinder that has a surrounding wall 241' in frictional contact with an inner surface of the syringe barrel 2', and a ring-shaped rear end wall 242' sleeved around and clamping a rear end of a needle holder 30' of the needle unit 3' therein. The central bore 310' in the needle unit 3' has an enlarged rear bore portion 304' that has a greatest diameter slightly greater than that of a rear opening 300' in the needle holder 30'. A holder-retaining front portion 51' of the sealing member 5' includes a fixed flexible insert member 510' that is movable within the syringe barrel 2' to engage fittingly the enlarged rear bore portion 304' of the central bore 310' in the needle unit 3' so as to retain the needle holder 30' on the sealing member 5'. The plunger 4' has a front end portion with an inward flange 44' that is configured as an annular rib which presses against a sealing rear portion 52' of the sealing member 5'. As such, the sealing member 5' can be removed forcibly from the plunger 4' for evacuation of air from the plunger 4'. The syringe barrel 2' has a front end wall 21' that is formed with a tapered front opening 210'. The needle unit 3' includes the needle holder 30', from which an outward flange similar to that in the previous embodiment is omitted, a needle 31', a spacer portion 32', and a connecting portion 33'. An assembly of the spacer portion 32' and the connecting portion 33' is shaped as a truncated cone. The connecting portion 33' extends through the front opening 210' in the syringe barrel 2' The spacer portion 32' is sized to prevent movement into the front opening 210'.

Figure 10:
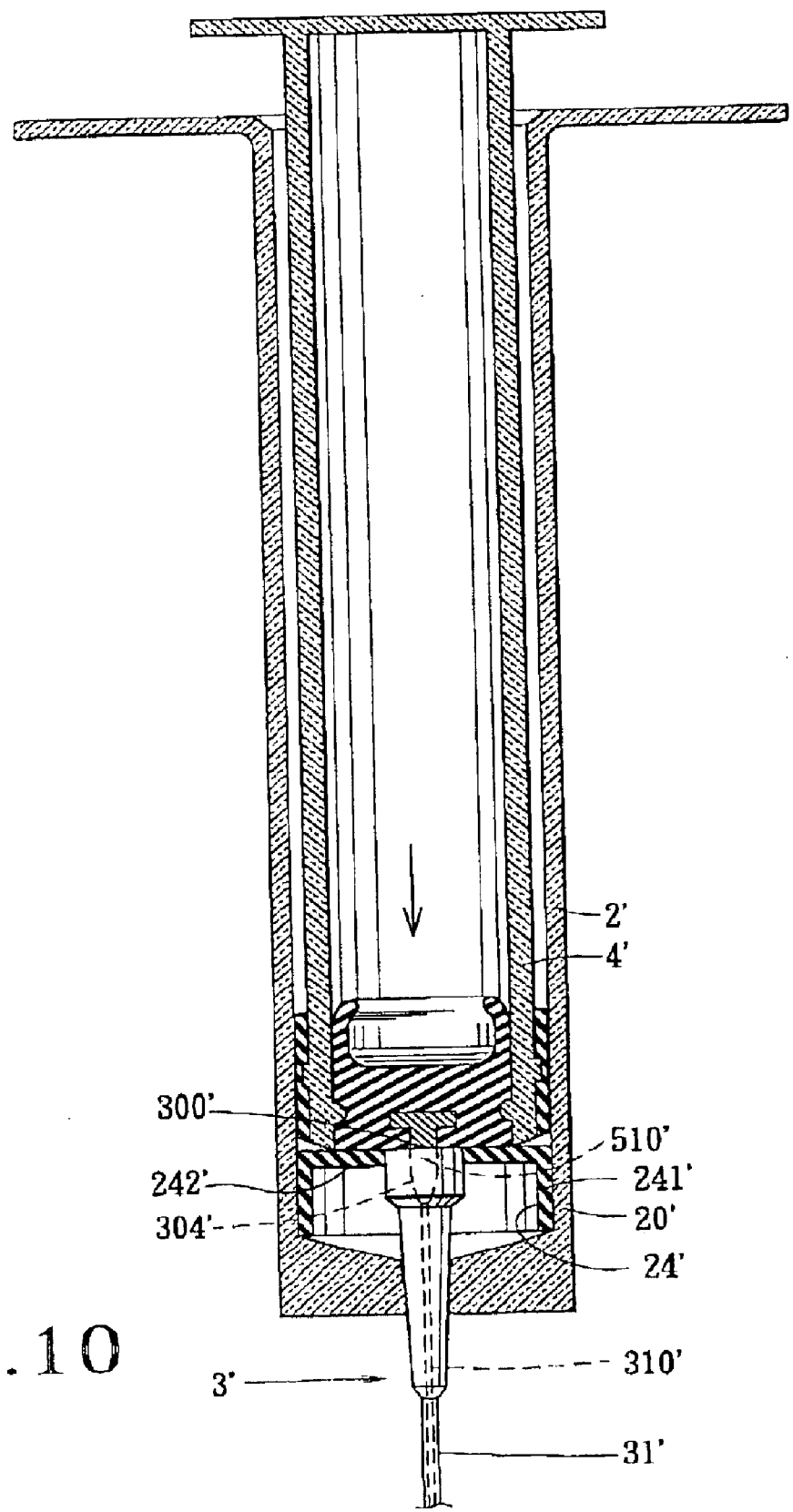
FIG. 10 illustrates how a holder-retaining front portion of a sealing member of the second preferred embodiment engages a needle holder.

The plunger 4' is movable forward within the syringe barrel 2' to a position shown in FIG. 10, where the insert member 510' engages the enlarged bore portion 304' of the central bore 310' in the needle unit 3' so as to prevent further forward movement of the sealing member 5' within the syringe barrel 2' and where a front end of the plunger 4' comes into contact with the rear end wall 24'.

Figure 11:
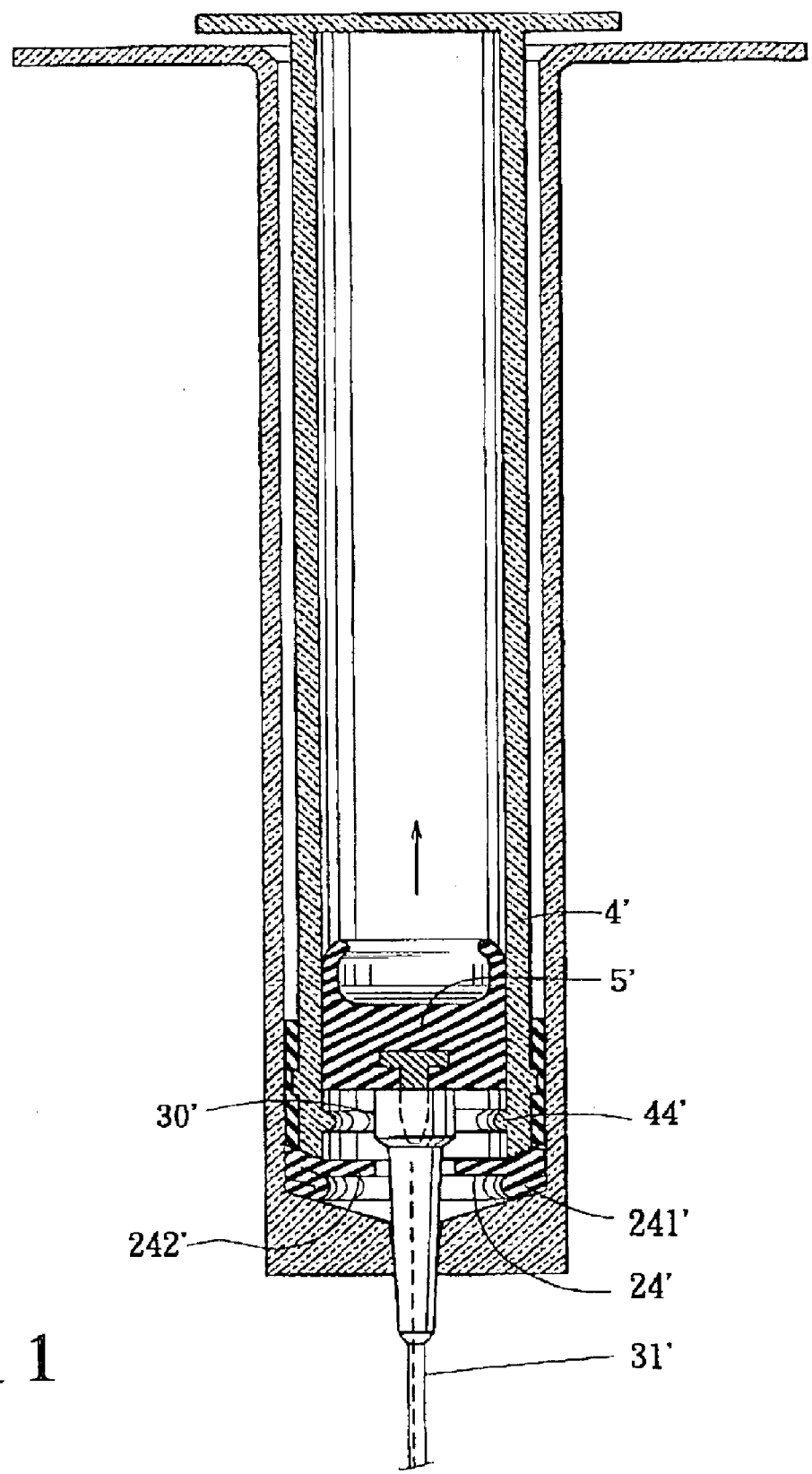
FIG. 11 illustrates how a holder-supporting seat of the second preferred embodiment is pushed by a plunger to separate from the needle holder.
Figure 12:
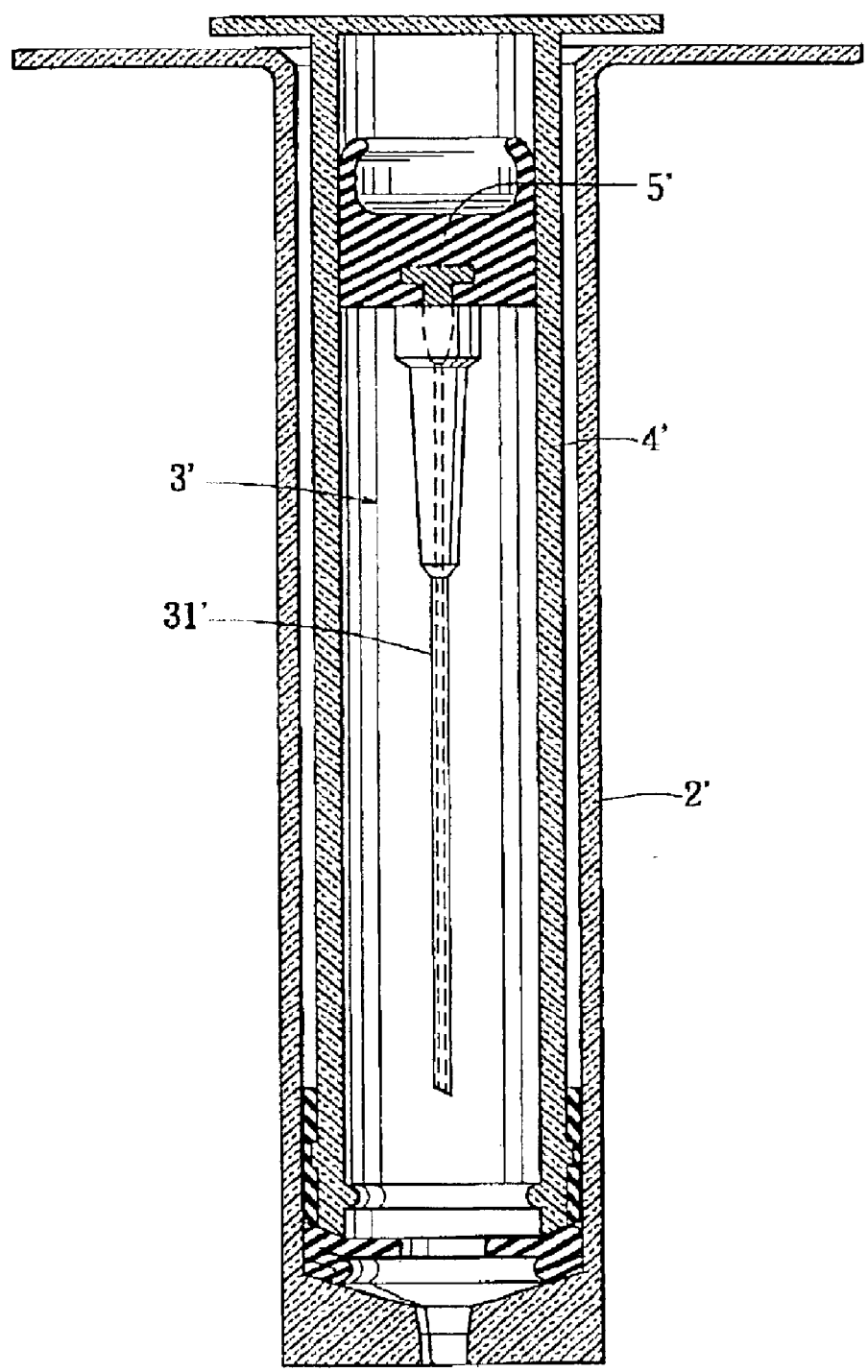
FIG. 12 illustrates how a needle unit of the second preferred embodiment is retracted into the plunger.

The plunger 4 will continue to move forward within the syringe barrel 2' to a front limit position shown in FIG. 11, where the inward flange 44' separates from the sealing member 5' and where the surrounding wall 241' of the holder-supporting seat 24' deforms to permit forward removal of the rear end wall 242' from the needle holder 30'. As such, the needle unit 3' can also be drawn into the plunger 4' due to negative pressure produced in the plunger 4'.

With this invention thus explained, it is apparent that numerous modifications and variations can be made without departing the scope and spirit of this invention. It is therefore intended that this invention be limited only as indicated by the appended claims.

I claim:

1. A safety syringe comprising:
   a syringe barrel having a front end wall with a front opening, and a rear end wall with a rear opening;
   a plunger disposed movably within said barrel and having a front end and a rear end that extends from said rear opening in said syringe barrel; and
   a needle unit extending through said front opening in said syringe barrel and including a central bore formed therethrough, a needle holder that is formed with a rear opening, and a needle that is connected fixedly to said needle holder at a rear end and that is exposed outwardly from said front opening in said syringe barrel;
   wherein said syringe barrel includes an annular flexible holder-supporting seat disposed movably within said syringe barrel and sleeved around said needle holder, said holder-supporting seat having a central hole formed therethrough, an outer periphery that is in frictional contact with an inner surface of said syringe barrel in such a manner that a liquid-tight seal is established therebetween, and an inner periphery that is in frictional contact with an outer surface of said needle holder in such a manner that a liquid-tight seal is established therebetween;

wherein said plunger has an open front end that is formed with a front opening, a rear end wall, and a front end portion that is formed with an inward flange extending integrally, radially, and inwardly therefrom;

wherein said safety syringe further comprises a flexible sealing member disposed movably within said front end portion of said plunger so as to define a vacuum chamber in said plunger between said sealing member and said rear end wall of said plunger, said inward flange being sleeved around and clamping said sealing member in said plunger so as to prevent movement of said sealing member relative to said plunger, thereby permitting synchronous rearward movement of said sealing member and said plunger when said plunger is pulled rearward relative to said syringe barrel, said sealing member having a holder-retaining front portion that is disposed behind and that is spaced apart from said needle holder, and a sealing rear portion for closing said front opening in said plunger;

wherein said needle unit has a spacer portion that is formed integrally between said needle holder and said needle and that is sized to prevent movement of said spacer portion into said front opening in said syringe barrel such that said needle holder is clamped within said holder-supporting seat at a position that is spaced apart from said front end wall by a predetermined distance;

wherein said holder-retaining front portion of said sealing member moves forward to retain said needle holder thereon, when said plunger is moved forward within said syringe barrel to push said holder-supporting seat forward, such that said holder-supporting seat separates from said needle holder so as to permit automatic rearward movement of an assembly of said sealing member and said needle unit within said syringe barrel due to negative pressure produced within said plunger, thereby retracting said needle into said syringe barrel.

2. The safety syringe as claimed in claim 1, wherein said needle unit is formed with an outward flange that extends integrally, radially, and outwardly from a rear end of said needle holder and that is sized to prevent forward movement of said outward flange into said central hole in said holder-supporting seat, said holder-retaining front portion of said sealing member being shaped as an annular flange that extends forwardly and inwardly to define a blind hole and that has a rounded front end edge for guiding movement of said outward flange of said needle holder into said blind hole, said blind hole including a front end that has a diameter which is slightly smaller than that of said outward flange of said needle unit so as to confine said outward flange within said blind hole when said outward flange moves into said blind hole.

3. The safety syringe as claimed in claim 2, wherein said holder-retaining front portion of said sealing member is formed with a curved projection that is located within said blind hole and that is movable within said syringe barrel to seal said rear opening in said needle holder when said outward flange engages said blind hole.

4. The safety syringe as claimed in claim 1, wherein said plunger includes a plunger body that has an open rear end so that said sealing member can be placed into said plunger body and can extend therethrough during assembly, said rear end wall of said plunger being unitary and having a circular projection that extends forwardly therefrom and that is press-fitted within said rear end of said plunger body so as to be removable form said plunger body.

5. The safety syringe as claimed in claim 1, wherein said holder-supporting seat is constructed as a hollow cylinder that has a surrounding wall in frictional contact with said inner surface of said syringe barrel, and a ring-shaped rear end wall sleeved around and clamping a rear end of said needle unit having an enlarged rear bore portion that has a greatest diameter slightly greater than that of said rear opening in said needle holder, said holder-retaining front portion of said sealing member including a fixed flexible insert member that is movable within said syringe barrel to engage fittingly said enlarged rear bore portion of said central bore so as to retain said needle holder on said sealing member.

* * * * *